United States Patent [19]
McKibben

[11] Patent Number: 4,554,489
[45] Date of Patent: Nov. 19, 1985

[54] RESONANT MAGNETIC DEFLECTION CIRCUIT

[75] Inventor: Barry A. McKibben, Beaverton, Oreg.

[73] Assignee: Tektronix, Inc., Beaverton, Oreg.

[21] Appl. No.: 449,070

[22] Filed: Dec. 13, 1982

[51] Int. Cl.⁴ .......................................... H01J 29/70
[52] U.S. Cl. ................................... 315/399; 315/395
[58] Field of Search .............. 315/395, 396, 397, 399, 315/388, 408, 398; 307/514

[56] References Cited

U.S. PATENT DOCUMENTS 3,988,637 10/1976 Boekhorst ........................... 315/393
4,464,612 8/1984 Teuling ............................... 315/408

FOREIGN PATENT DOCUMENTS 2072983 7/1981 United Kingdom ............... 315/408

OTHER PUBLICATIONS

Electronic Engineers Handbook, Sec. 20-71 through 20-73, pp. 20-52 to 20-53, FIGS. 20-53.

Primary Examiner—Theodore M. Blum
Assistant Examiner—Gregory C. Issing
Attorney, Agent, or Firm—John H. Bouchard; Francis I. Gray

[57] ABSTRACT

A resonant magnetic deflection circuit is disclosed for reducing a retrace period of an electron beam scanning within a cathode ray tube (CRT) apparatus. Opposite polarity flyback voltage pulses occur at both ends of a deflection coil. As a result, an effective retrace voltage appearing across the deflection coil is approximately doubled, thereby reducing the retrace period of the electron beam scanning within the CRT apparatus. One end of the deflection coil is connected to a reference level source through a first parallel circuit and an S-correction capacitor, the other end thereof being connected to the reference level source through a second parallel circuit. The first and second parallel circuits comprise switching devices, damper diodes and retrace capacitors. Moreover, both ends of the deflection coil are connected to a power supply through a flyback transformer.

15 Claims, 5 Drawing Figures

RESONANT MAGNETIC DEFLECTION CIRCUIT

BACKGROUND OF THE INVENTION

The present invention generally relates to a resonant magnetic deflection circuit, more particularly, to a horizontal magnetic deflection circuit for a raster scan type cathode ray tube display apparatus.

A raster scan type cathode ray tube (CRT) display is widely used as a picture monitor, or as a display apparatus in a computer display terminal, or the like. For displaying an image on the CRT, an electron beam generated therein is scanned across the CRT, and, simultaneously therewith, is modulated and deflected in a horizontal and a vertical direction. There are two types of deflection circuits. One of the circuits is an electrostatic deflection circuit, the other being an electromagnetic deflection circuit. The latter is popular for the raster scan type display apparatus in comparison with the former because of its high deflection efficiency. In the magnetic deflection circuit, a ramp current flows through a yoke, namely, a deflection coil. A resonant magnetic deflection circuit is generally used as a horizontal deflection circuit. A conventional resonant magnetic deflection circuit is disclosed on pages 20-52 and 20-53 of "Electronics Engineer's Handbook, First Edition" edited by Donald G. Fink and published by McGraw-Hill Book Company in 1975. This conventional resonant magnetic deflection circuit comprises a switching transistor controlled in accordance with a horizontal drive signal, a damper diode and a retrace capacitor connected in parallel with the switching transistor, a series circuit consisting of a deflection coil, an S-correction large capacitor connected in series with the switching transistor, and a voltage source connected to a common junction of these devices through an inductor, such as a flyback transformer. The retrace capacitor and the deflection coil form a resonant circuit, so that energy from a power supply is converted to an electromagnetic energy of the deflection coil for the latter half of a scanning (trace) period, the electromagnetic energy being converted to electrostatic energy of the retrace capacitor for the first half of a retrace period, the electrostatic energy being converted to the electromagnetic energy again for the latter half of the retrace period, the electromagnetic energy returning to the power supply for the first half of the scanning period. Thus, efficiency is very high. Moreover, a deflection coil and an S-correction capacitor comprises a resonant circuit for correcting S-distortion. Therefore, the resonant magnetic deflection circuit is widely used.

On the other hand, the inductance (Ly) of the deflection coil is determined by the power voltage (Vc), the scanning period (ts) and the deflection efficiency (E), i.e., $Ly=(Vc \cdot ts)^2/E$. The retrace period tR is defined to be equal to $\pi\sqrt{LyC_R}$, wherein $C_R$ is the capacitance connected in parallel with the series circuit including the deflection coil. It is desirable to reduce the retrace period, because the scanning period can be increased as a result thereof, since the sum of the scanning and retrace periods is determined to be a horizontal period (for example, 63.5 µs) of a video signal standard. Thus, the retrace period directly affects video bandwidth and CRT brightness requirements. If these requirements are reduced, it may be easy to manufacture a very high resolution video display apparatus.

As described hereinbefore, the retrace period is determined by the variables Ly and $C_R$, the variable $L_y$ being determined by many factors. The retrace period can be reduced by decreasing the capacitance $C_R$.

When Ly energy is transferred completely to $C_R$, then $\frac{1}{2}LyI^2 = \frac{1}{2}C_RV^2$, I=peak deflection current (determined by other factors), V=peak voltage across $C_R$. Since $t_R = \pi\sqrt{LyC_R}$, it follows that $$V = \frac{ILy\pi}{t_R}.$$

The peak voltage across $C_R$ then increases in proportion to $1/t_R$. Therefore, the retrace capacitor, deflection yoke, switching device, damper diode, flyback transformer, and all other circuit elements connected to the retrace capacitor must withstand the higher peak voltage if retrace period is to be reduced by decreasing $C_R$.

However, the flyback transformer has a large stray capacitance, and the capacitance of variable $C_R$ is determined by a sum of the stray capacitance and the retrace capacitor's capacitance. The capacitance variable $C_R$ cannot be less than the stray capacitance. If the retrace capacitor is removed from the deflection circuit, the capacitance $C_R$ may be unstable. Thus, it is difficult to reduce the retrace period by decreasing the capacitance $C_R$.

In a higher resolution raster type display and in a stroke-writing type CRT display, a deflection yoke contains two physically separate, series connected, horizontal windings (deflection coils) with a core and vertical windings adjacent to both the horizontal windings. A horizontal retrace pulse of the resonant deflection circuit can produce a damped oscillation in the vertical windings. This phenomenon is called "yoke ringing". This "yoke ringing" can appear on a display screen as a set of wavey horizontal lines.

SUMMARY OF THE INVENTION

According to the present invention, parallel circuits each consisting of a switching device, such as a transistor, a damper diode and a retrace capacitor, are connected to both ends of a horizontal deflection coil (yoke), which are connected to a power supply through a flyback transformer. An S-correction large capacitor is connected to the other end of one of the parallel circuits, and both the switching devices are simultaneously controlled by a drive pulse. Since a flyback pulse occuring at one end of the deflection coil is opposite in polarity to a flyback pulse at the other end of the deflection coil, the effective retrace voltage across the deflection coil is twice what it would be in a conventional deflection circuit. Thus, the present invention can reduce the retrace period without increased voltage or current in the switching devices, damper diodes and retrace capacitors, and without increasing the insulation requirements of the yoke. Moreover, the present invention can reduce "yoke ringing" because symmetrical drive of the horizontal windings reduces the tendency to excite self-resonant oscillations in the vertical windings.

If storage times of the switching transistors of the present invention are different from each other, the two switching transistors may not operate simultaneously. Especially, the off times thereof may be different, and the flyback pulses at both the ends of the deflection coil are not symmetrical. This affects the retrace period and "yoke ringing". The present invention solves this problem by applying a horizontal drive signal to the bases of the switching transistors through a variable delay circuit and a fixed delay circit. A phase comparator compares the two flyback pulses and controls the variable delay circuit so that the flyback pulses occur simultaneously.

The present invention further includes a floating variable current source that establishes a direct current in the yoke through the flyback transformer and functions as a centering adjustment or position control.

It is therefore one object of the present invention to provide a novel resonant magnetic deflection circuit for a raster scan type CRT display apparatus.

It is another object of the present invention to provide a resonant magnetic deflection circuit which reduces a retrace period without increasing a voltage or current in associated devices and without increasing the insulation requirements of a yoke.

It is a further object of the present invention to provide a resonant magnetic horizontal deflection circuit which reduces "yoke ringing".

It is an additional object of the present invention to provide a resonant magnetic deflection circuit which allows for differences in storage times of two switching transistors.

It is another object of the present invention to provide a resonant magnetic deflection circuit which includes a floating variable current source for providing a centering adjustment or position control.

Other objects, advantages, and features of the present invention will become apparent to those having ordinary skill in the art from a reading of the following detailed description when taken in conjunction with the accompanying drawings.

BRIEF DESCRIPTION OF THE DRAWINGS

A full understanding of the present invention will be obtained from the detailed description given hereinbelow and the accompanying drawings, which are given by way of illustration only, and thus are not limitative of the present invention, and wherein.

DETAILED DESCRIPTION OF THE INVENTION

Figure 1:
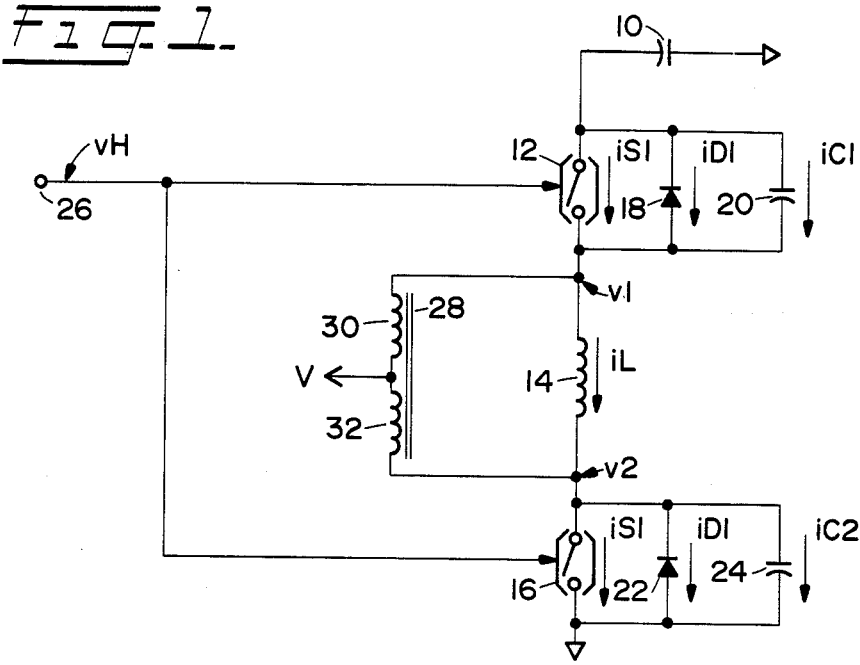
FIG. 1 illustrates a block diagram of one preferred embodiment of a resonant magnetic deflection circuit according to the present invention.

Referring to FIG. 1, there is shown a basic block diagram of a resonant magnetic deflection circuit according to the present invention. A series circuit consisting of an S-correction large capacitor 10 (e.g. 0.66 μF), switching device 12, horizontal deflection coil (winding) 14 and switching device 16 is connected to a reference level which may be ground potential. Damper diode 18 and retrace capacitor 20 are connected in parallel with switching device 12, damper diode 22 and retrace capacitor 24 being connected in parallel with switching device 16. Switching devices 12 and 16 may be switching transistors, and are controlled by a horizontal drive signal at terminal 26. As is well known, the horizontal drive signal is generated by a synchronizing circuit (not shown) in accordance with a horizontal synchronizing signal. Both ends of deflection coil 14 are connected to voltage power supply V through windings 30 and 32 of flyback transformer 28. If the upper end of deflection coil 14 is directly connected to capacitor 10 and winding 30 is removed, the resultant circuit of FIG. 1 would be a conventional resonant magnetic deflection circuit.

Figure 2:
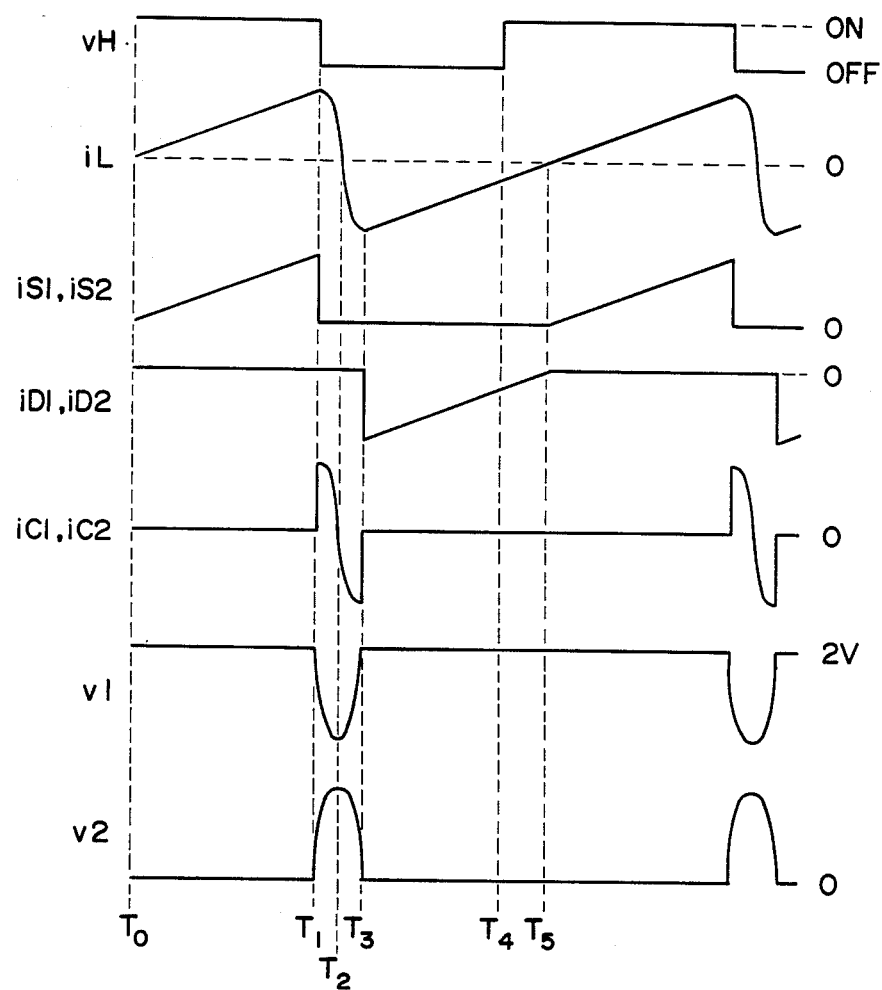
FIG. 2 illustrates a time chart for explaining the operation of FIG. 1.

The operation of FIG. 1 will be discussed by reference to a time chart of FIG. 2. Power energy is supplied from voltage power supply V through flyback transformer 28. Since voltages $V_1$ and $V_2$ at the upper and lower ends of deflection coil 14 are symmetrically opposed because of the function of flyback transformer 28, and since during the scanning period, the voltage $V_2$ is nearly a ground potential, therefore, during the scanning period, the voltage $V_1$ must be nearly two times the power voltage V. Thus, the voltage on capacitor 10 is 2 V. During the operation, the average voltage of flyback transformer 28 and deflection coil 14 is the power voltage V (assuming lossless inductors). Also, for purposes of the discussion, assume capacitor 10 is large enough that its voltage does not vary during the operation. At a time $T_0$, a horizontal drive signal $V_H$ is "High", and switching devices 12 and 16 are on. Thus, the voltages $V_1$ and $V_2$ are respectively 2 V and ground level. A current $i_L$ flowing through deflection coil 14 is determined by the inductance L of coil 14 and the voltage thereof, i.e., $di_L = (2V/L)\,dt$. Thus, the current $i_L$ is a positive going linear ramp waveform. Since the current $i_L$ flows from capacitor 10 via switching device 12, coil 14 and switching device 16 to capacitor 10, currents $i_{S1}$ and $i_{S2}$, flowing through switching devices 12 and 16, are the same as the current $i_L$. No current flows through damper diodes 18 ($i_{D1}$) and 22 ($i_{D2}$) and retrace capacitors 20 ($i_{C1}$) and 24 ($i_{C2}$) during this period. Deflection coil 14 stores electromagnetic energy. At a time $T_1$, the horizontal drive signal $V_H$ changes from "High" to "Low", and switching devices 12 and 16 turn off. Because of the characteristics of inductor 14, the current $I_L$ flows in the same direction and charges retrace capacitors 20 and 24, i.e., the electromagnetic energy of deflection coil 14 is transferred to capacitors 20 and 24 as electrostatic energy. The current $i_L$ decreases and voltages across capacitors 20 and 24 increase as the time proceeds because of the resonance of deflection coil 14 and capacitors 20 and 24. At a time $T_2$, the current $i_L$ reduces to zero, and the voltages across capacitors 20 and 24 are at their peak values, and all of the electromagnetic energy is converted to electrostatic energy. Therefore, the voltages $V_1$ and $V_2$ are also at their peak values. The amplitudes thereof are equal, but the polarities thereof are opposite with respect to one another. It should be noted that the polarities of windings 30 and 32 of flyback transformer 28 are symmetrical. The voltages $V_1$ and $V_2$ are called flyback (retrace) pulses. After the time $T_2$, retrace capacitors 20 and 24 discharge through deflection coil 14, and the electrostatic energy thereof is converted into electromagnetic energy. The voltages $V_1$ and $V_2$ decrease and the current $i_L$ increases in the opposite direction as time proceeds because of resonance. At a time $T_3$, the current $i_L$ reaches a negative peak value, and the voltages $V_1$ and $V_2$ return to their stable levels. The currents $i_{C1}$ and $i_{C2}$ are the same as the current $i_L$ during the period between the times $T_1$ and $T_3$. After the time $T_3$, the current $i_L$ flows through damper diodes 18 and 22 in the opposite direction because of the counter electromotive force of deflection coil 14, and the current $i_L$ reduces linearly to zero at a time $T_5$. Thus, the electromagnetic energy returns to capacitor 10. The horizontal drive signal $V_H$ changes from "Low" to "High" to turn on switching devices 12 and 16 at time $T_4$. Since switching devices 12 and 16 are unilateral devices, the current $i_L$ flows through diodes 18 and 22 for the period between the times $T_3$ and $T_5$. The operation after the time $T_5$ is the same as the operation between the times $T_0$ and $T_5$.

As described hereinbefore, the flyback pulses $V_1$ and $V_2$ occur at both ends of deflection coil 14, in opposite polarities, so that the effective retrace voltage across deflection coil 14 is twice what it would be in a conventional circuit and the retrace (between the times $T_1$ and $T_3$) is accomplished in half the time. For example, the present invention allows for a reduction in horizontal retrace time from 33% of the horizontal period to 17% allowing for a 23% reduction in video bandwidth and provides a 23% increase in luminance. Therefore, the present invention is suitable for a high resolution video display apparatus.

If the voltage on S-correction capacitor 10 drops, then the average voltage of deflection coil 14 also drops causing a current to be drawn from voltage power supply V through flyback transformer 28 until the voltage on capacitor 10 again reaches 2 V. In actuality, the voltage on capacitor 10 varies during the above-described operation (to achieve linearity correction), although its average voltage remains 2 V. This variation is superimposed on the operation described above without changing the basic principle of operation of the present invention.

Figure 3:
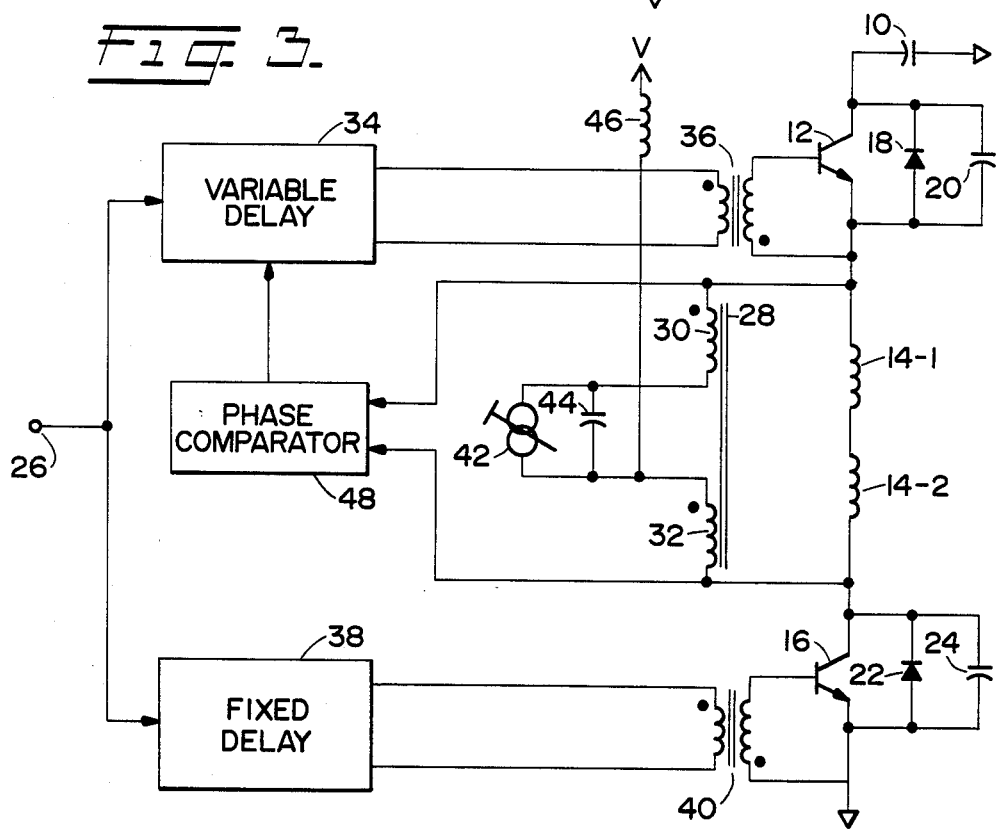
FIG. 3 illustrates a block diagram of another embodiment of a resonant magnetic deflection circuit according to the present invention.

FIG. 3 illustrates a block diagram of another embodiment of the present invention, wherein this embodiment is similar to that of FIG. 1, so that the same reference numbers have been employed to designate like parts, only the differences therebetween will be discussed. The deflection coil consists of two coils 14-1 and 14-2 connected in series between switching devices 12 and 16 which are bipolar transistors. The base of switching transistor 12 receives a horizontal drive signal from terminal 26 through variable delay circuit 34 and transformer 36. Similarly, the base of transistor 16 receives the horizontal drive signal via fixed delay circuit 38 and transformer 40. A parallel circuit consisting of floating variable current source 42 and capacitor 44 is inserted between windings 30 and 32 of flyback transformer 28, and the common junction of the parallel circuit and winding 32 is connected to voltage source V through inductor 46. Phase comparator 48 receives the voltages at the emitter of transistor 12 and the collector of transistor 16 and controls the delay time of variable delay circuit 34.

It is desirable to match the characteristics of transistor 12 to that of transistor 16. However, such a match is difficult to achieve. If storage times of transistors 12 and 16 are different from each other, the turn off times of transistors 12 and 16 may be different from each other, if the transistors receive the horizontal drive signal simultaneously. This affects the flyback pulses, i.e., the pulses may not occur simultaneously and therefore may not be symmetrical. Thus, the retrace period may not be reduced effectively. This disadvantage is overcome by delay circuits 34 and 38 and phase comparator 48. Fixed delay circuit 38 delays the horizontal drive signal by a predetermined time, and the delay time of variable delay circuit 34 is within a predetermined range including the delay time of delay circuit 38. Phase comparator 48 compares the phase of the flyback pulse at the collector of transistor 16, and controls the delay time of variable delay circuit 34 in accordance with the phase differences so that both the flyback pulses start simultaneously, i.e., transistors 12 and 16 turn off simultaneously. Thus, the present invention allows for differences in storage time between transistors 12 and 16, and the retrace period can be reduced effectively regardless of the storage time difference between transistors 12 and 16. Blocks 34, 38, and 48 illustrated in FIG. 3 will be further discussed hereinafter with reference to FIG. 4 of the drawings.

Floating variable current source 42 establishes a direct current in deflection coils 14-1 and 14-2 via flyback transformer 28, and functions as a centering adjustment or position control. In other words, the current from variable current source 42 flows through winding 30, coils 14-1 and 14-2 and winding 32, and returns to current source 42. This current acts as a bias. As described hereinabove, the voltage applied to deflection coils 14-1 and 14-2 during the scanning period is not constant but varies somewhat due to the action of S-correction capacitor 10. This S-correction waveform is also present at the center terminals of flyback transformer 28 (although its amplitude is reduced to half). Inductor 46 is therefore necessary to decouple this waveform from power supply V. In addition, due to leakage reactance variations between two windings 30 and 32 of flyback transformer 28, the equal and opposite retrace pulse at the end terminals of flyback transformer 28 may not precisely cancel at the center terminals thereof. Capacitor 44 is present to absorb any resulting voltage transient so that the voltage compliance requirements of current source 42 may be kept small. On the other hand, the purpose of transformer 28 is to supply power to switching transistors 12 and 16 and centering current to deflection coils 14-1 and 14-2 while preventing the retrace pulses from reaching current source 42 and power supply V. The current source 42 and the power supply will be described hereinafter with reference to FIG. 5.

When a yoke contains two physically separate, series connected, horizontal deflection coils with a core and vertical deflection coils adjacent to both the horizontal deflection coils, the horizontal retrace pulse may excite a damped oscillation in the vertical deflection coils (yoke ringing). However, the present invention may reduce "yoke ringing", because the symmetrical drive of horizontal deflection coils reduces the tendency to excite self-resonant oscillations in the vertical deflection coils.

Figure 4:
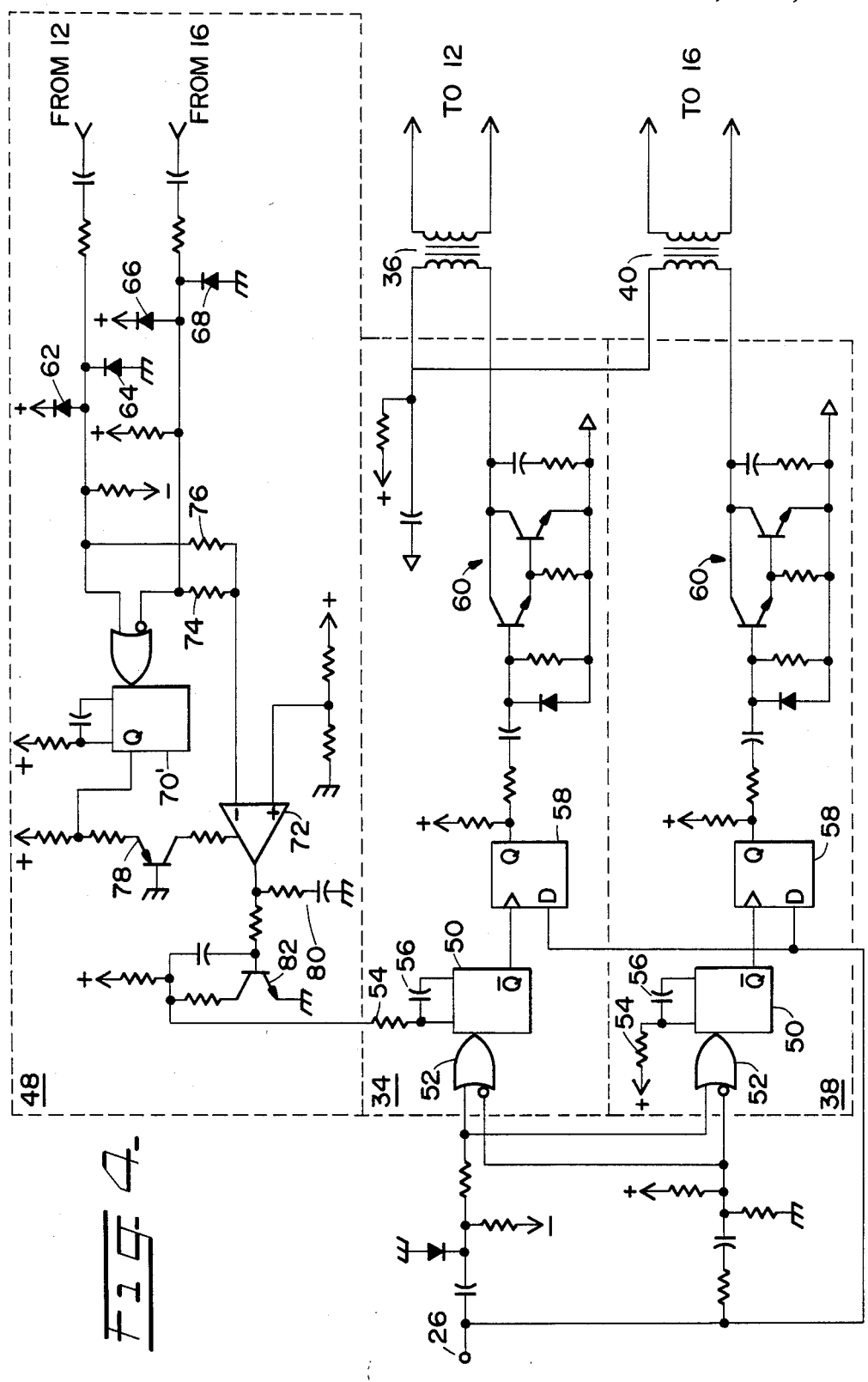
FIG. 4 illustrates a circuit schematic of variable and fixed delay circuits and a phase comparator used in FIG. 3.

Referring to FIG. 4, delay circuits 34 and 38 and phase comparator 48 will be explained in detail hereinafter. In variable delay circuit 34, monostable multivibrator 50 is triggered by both the rising and falling edges of the horizontal drive signal at terminal 26 because of OR gate portion 52. Multivibrator 50 includes a time constant circuit consisting of timing resistor 54 and timing capacitor 56. After a short delay, the $\overline{Q}$ output signal of monostable multivibrator 50 clocks D flip-flop 58 which passes the current state of the horizontal drive signal to drive circuit 60 consisting of two transistors and associated devices. The output signal from drive circuit 60 controls switching transistor 12 through transformer 36. Thus, variable delay circuit 34 delays the horizontal drive signal by a time determined by resistor 54, capacitor 56, and a voltage applied to resistor 54. Since resistor 54 receives the output signal from phase comparator 48, comparator 48 is allowed to control the delay time of delay circuit 34. Multivibrator 50 and flip-flop 58 may respectively comprise type 9602 and 7474 integrated circuits (ICs). For example, resistor 54 is 20 K-ohm and capacitor 56 is 470 pF.

Fixed delay circuit 38 is identical to variable delay circuit 34 execept that the voltage applied to resistor 54 is constant (e.g. +5 v). In the embodiment, resistor 54 is different from variable delay circuit 34, and is 10 K-ohm.

In phase comparator 48, the flyback pulses at the emitter of transistor 12 and the collector of transistor 16 are reduced in amplitude to TTL levels by clamping diodes 62 through 68, and applied to the input terminals of monostable multivibrator 70 and gated transconductance amplifier 72. Multivibrator 70 is triggered by both the flyback pulses because of an OR gate function, and amplifier 72 receives the average value of both the flyback pulses converted to the TTL Levels because of the same resistors 74 and 76. Multivibrator 70 and amplifier 72 may respectively comprise type 9602 and 3080 Integrated Circuits. Whichever flyback pulse occurs, the first pulse triggers monostable multivibrator 70 which then enables amplifier 72 for about 200 ns via common-base transistor 78. If the flyback pulses occur simultaneously, one pulse is positive going and the other one is negative going, then the signal at the inverting input terminal of amplifier 72 is unchanged. If the positive going flyback pulse occurs first, then the inverting input terminal is pulled positive until the negative going pulse arrives. If the negative going pulse is first, the inverting input terminal of amplifier 72 is pulled to ground. Since amplifier 72 is gated to respond to the input signal for only a short time after the leading edge of the earliest flyback pulse, any difference in arrival time causes a corresponding signal at the output terminal of amplifier 72. This signal is smoothed by filter 80, and amplified by common-emitter transistor 82. The output signal from transistor amplifier 82 is applied to timing resistor 54 of variable delay circuit 34. The overall effect is that the flyback pulses are made to occur simultaneously in spite of unequal storage times of transistors 12 and 16.

Figure 5:
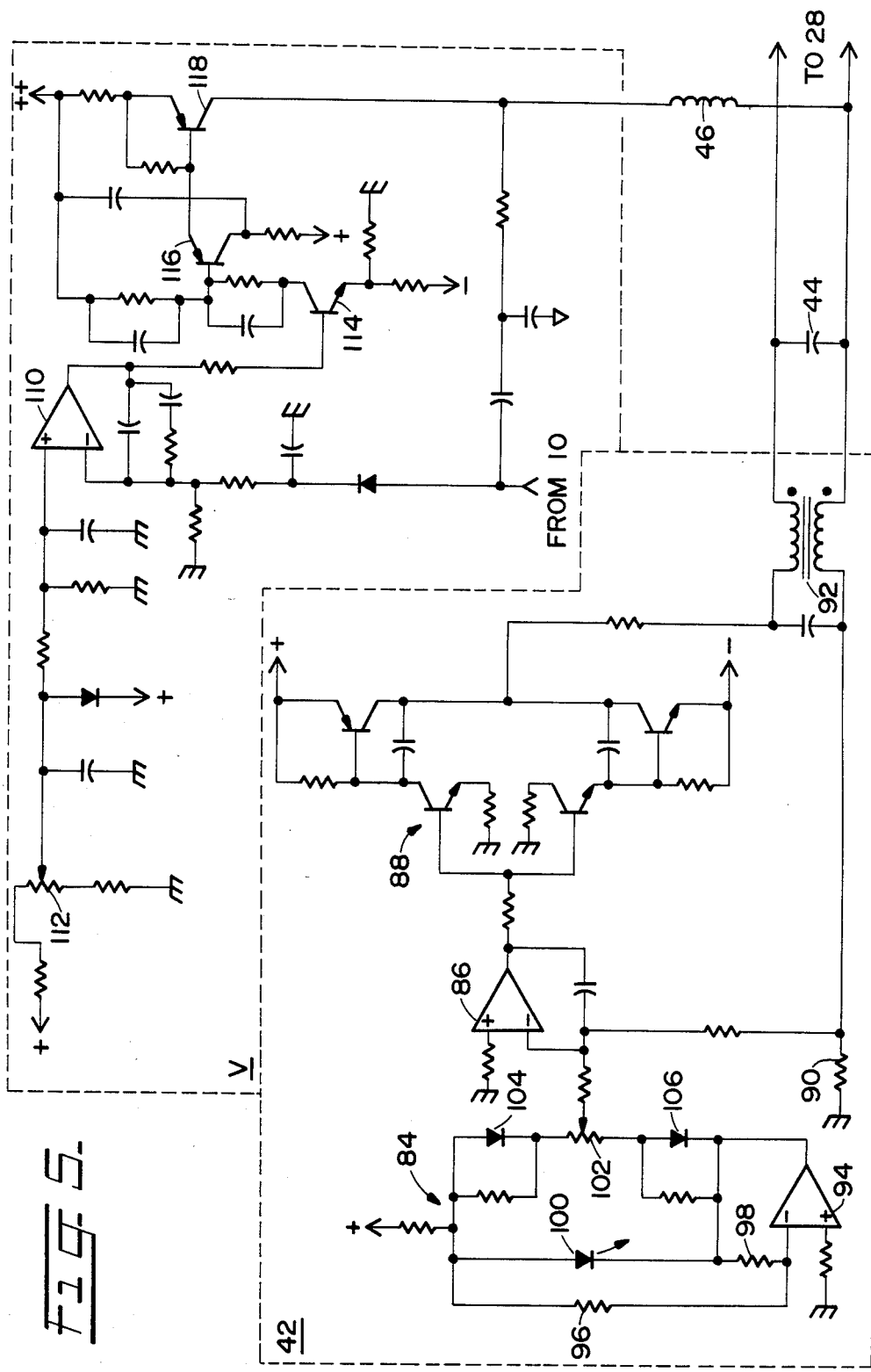
FIG. 5 illustrates a circuit schematic of a floating variable current source and a power supply used in the block diagram of FIG. 3.

FIG. 5 illustrates a circuit schematic of floating variable current source 42 and power supply V of FIG. 3. Floating variable current source 42 comprises variable voltage source 84, operational amlifier 86, buffer amplifier 88 for amplifier 86, current detection resistor 90 and transformer 92 for improving a common mode rejection ratio. Since variable voltage source 84 includes operational amplifier 94 having input resistor 96 and feedback resistor 98, the output voltage of amplifier 94 is negative. Light emission diode (LED) 100 acts as a zener diode, and both the ends of potentiometer 102 receive symmetrical positive and negative voltages. Diodes 104 and 106 are provided for temperature compensation. A feedback current flows from deflection coils 14-1 and 14-2 through transformers 28 and 92 to current detection resistor 90, so that the voltage across resistor 90 is proportional to the feedback current. The difference between the voltages at potentiometer 102 and resistor 90 is divided and applied to the inverting input terminal of amplifier 86. Amplifier 86 drives buffer 88 to supply the output current so that the divided voltage at the inverting input terminal is equal to floating ground level. Thus, the output current may be controlled by potentiometer 102. Amplifiers 84 and 94 may be type 358 Integrated Circuits.

Power supply "V" of FIG. 5 acts as a current source which includes operational amplifier 110 with the non-inverting input terminal receiving a variable voltage from potentiometer 112 and the inverting input terminal receiving a feedback voltage from S-correction capacitor 10. The output signal from amplifier 110 is amplified by transistors 114 and 116, and drives current source transistor 118. The function of inductor 46 is performed by power supply "V" which is a high compliance current source. As a result of the feedback path, amplifier 110 controls the voltage on S-correction capacitor 10 by varying the current from transistor 118. Since the peak deflection current is proportional to the voltage on capacitor 10, a picture width is controlled by potentiometer 112 and is varied dynamically to achieve a side pincushion correction.

As described hereinbefore, the present invention reduces the retrace period without increasing voltage or current in the switching devices, damper diodes, retrace capacitors, and without increasing insulation requirements of the deflection coils. Moreover, the present invention may reduce "yoke ringing".

While I have shown and described herein the preferred embodiments of my invention, it will be apparent to those skilled in the art that many changes and modifications may be made without departing from my invention in its broader aspects. For example, the switching device may be a field effect transistor, and the present invention may be used as a vertical deflection circuit. In addition, the present invention may be applied to a deflection circuit of a scan conversion tube, image pickup tube, electron microscope or the like. The retrace capacitors may be removed, and the stray capacitance of the flyback transformer may act as the retrace capacitance. Therefore, the scope of the present invention should be determined only by the breadth of the following claims.

What I claim as being novel is:

1. A resonant magnetic deflection circuit comprising:
   a deflection coil;
   means controlled by a drive signal for developing a first flyback voltage pulse at one end of said deflection coil and a second flyback voltage pulse, having a polarity opposite to said first flyback voltage pulse, at the other end of said deflection coil;
   means for variably delaying said drive signal;
   means for fixedly delaying said drive signal; and
   means for comparing said flyback voltage pulses to provide a compensation signal to said variably delaying means so that the delayed drive signals from said variably and fixedly delaying means are applied to said developing means to cause said flyback voltage pulses occur simultaneously.

2. A resonant magnetic deflection circuit, comprising:
   a first parallel circuit including a switching device and a diode;
   a second parallel circuit including a switching device and a diode;
   a deflection coil connected to one terminal of said first parallel circuit and to one terminal of said second parallel circuit;
   a capacitor connected to the other terminal of said first parallel circuit;
   a transformer having two windings connected between a power supply and said one terminal of said first and second parallel circuits, said switching device of said first and second parallel circuits being controlled in accordance with a drive signal;
variable and fixed delay circuit means for delaying said drive signal; and
phase comparator means for comparing pulses occurring at said one terminal of said first and second parallel circuits and for controlling said variable delay circuit means in accordance with a phase comparison result.

3. A resonant magnetic deflection circuit according to claim 2, wherein said first and second parallel circuits include capacitors.

4. A resonant magnetic deflection circuit according to claim 2, wherein said switching devices are switching transistors.

5. A resonant magnetic deflection circuit according to claim 2 further including a variable current source inserted between said two windings of said transformer.

6. A resonant magnetic deflection circuit according to claim 5 further including a capacitor connected in parallel with said variable current source.

7. A resonant magnetic deflection circuit according to claim 5 further including an inductor inserted between said power supply and one of said two windings.

8. A resonant magnetic deflection circuit according to claim 4, wherein said switching transistors are controlled in response to a drive signal applied to a flyback transformer.

9. A resonant magnetic horizontal deflection circuit for a raster scan type display apparatus, comprising:
a circuit including an S-correction capacitor, first switching transistor, a deflection coil and a second switching transistor connected in series, both ends of said circuit being connected to a reference level source, said first and second switching transistors being controlled by a horizontal drive signal;
a first damper diode and a first retrace capacitor connected in parallel with said first switching transistor;
a second damper diode and a second retrace capacitor connected in parallel with said second switching transistor;
a transformer having two windings connected between a power supply and both terminals of said deflection coil;
variable and fixed delay circuit means for delaying said horizontal drive signal; and
phase comparator means for comparing pulses occurring at both terminals of said deflection coil and for controlling a delay time of said variable delay circuit means in accordance with a phase comparison result whereby said pulses occur simultaneously.

10. A resonant magnetic horizontal deflection circuit according to claim 9, further including:
a variable current source inserted between said two windings of said transformer;
a capacitor connected in parallel with said variable current source; and
an inductor inserted between said power supply and one of said two windings.

11. A resonant magnetic horizontal deflection circuit according to claim 9, wherein said deflection coil is divided into two portions.

12. A resonant magnetic deflection circuit as recited in claim 1 wherein said developing means comprises:
a circuit having a capacitor and a first switching circuit connected in series to one end of said deflection coil and a second switching circuit connected in series to the other end of said deflection coil, the ends of said circuit being connected to a reference level source, and said switching circuits being controlled by said selectively delayed drive signal; and
a transformer having two windings connected between a power supply and opposite ends of said deflection coil.

13. A resonant magnetic deflection circuit as recited in claim 12 wherein said switching circuits each comprise:
a switching device controlled by said selectively delayed drive signal; and
a damper diode connected in parallel with said switching device.

14. A resonant magnetic deflection circuit as recited in claim 13 wherein said switching circuits each further comprise a retrace capacitor connected in parallel with said switching device and damper diode.

15. A resonant magnetic deflection circuit as recited in claim 12 wherein said developing means further comprises:
a variable current source inserted between said windings;
a capacitor connected in parallel with said variable current source; and
an inductor inserted between said power supply and one of said windings.

* * * * *